(12) United States Patent
Ross et al.

(10) Patent No.: US 8,703,267 B2
(45) Date of Patent: Apr. 22, 2014

(54) SYNTHETIC GECKO ADHESIVE ATTACHMENTS

(75) Inventors: Russell Frederick Ross, Atlanta, GA (US); Ronald S. Fearing, Orinda, CA (US); Brian G. Bush, Emeryville, CA (US)

(73) Assignees: Kimberly-Clark Worldwide, Inc., Neenah, WI (US); The Regents of the University of California, Berkeley, CA (US)

( * ) Notice: Subject to any disclaimer, the term of this patent is extended or adjusted under 35 U.S.C. 154(b) by 429 days.

(21) Appl. No.: 12/938,756

(22) Filed: Nov. 3, 2010

(65) Prior Publication Data

US 2012/0107570 A1 May 3, 2012

(51) Int. Cl.
  B32B 3/00 (2006.01)
  B32B 37/12 (2006.01)
  B32B 37/14 (2006.01)

(52) U.S. Cl.
  USPC .............. 428/99; 428/100; 428/172

(58) Field of Classification Search
  USPC ........................... 428/99, 100, 172
  See application file for complete search history.

(56) References Cited

U.S. PATENT DOCUMENTS

| | | |
|---|---|---|
| 2,787,241 A | 4/1957 | Kelley |
| 3,397,697 A | 8/1968 | Rickard |
| 4,285,343 A | 8/1981 | McNair |
| 4,397,704 A | 8/1983 | Frick |
| 4,556,146 A | 12/1985 | Swanson et al. |
| 4,589,876 A | 5/1986 | Van Tilburg |
| 4,608,047 A | 8/1986 | Mattingly |
| 4,687,478 A | 8/1987 | Van Tilburg |
| 4,753,649 A | 6/1988 | Pazdernik |
| 4,834,739 A | 5/1989 | Linker, III et al. |
| 4,917,697 A | 4/1990 | Osborn, III et al. |
| 5,011,480 A | 4/1991 | Gossens et al. |
| 5,399,219 A | 3/1995 | Roessler et al. |
| 5,681,303 A | 10/1997 | Mills et al. |
| 5,766,389 A | 6/1998 | Brandon et al. |
| 6,143,135 A | 11/2000 | Hada et al. |
| 6,562,167 B2 | 5/2003 | Coenen et al. |

(Continued)

FOREIGN PATENT DOCUMENTS

WO   WO 9118574 A1   12/1991
WO   WO 03095190 A1   11/2003

OTHER PUBLICATIONS

Ko et al., "Hybrid Core—Shell Nanowire Forests as Self-Selective Chemical Connectors," *Nano Letters*, vol. 9, No. 5, 2009, pp. 2054-2058.

(Continued)

*Primary Examiner* — Brent O'Hern
(74) *Attorney, Agent, or Firm* — Dority & Manning, P.A.

(57) ABSTRACT

An adhesive material that contains a plurality of setae that include a stalk and spatula extending therefrom is provided. To form the adhesive material, a substantially planar substrate may be initially molded to define the setae. In this initial configuration, the setae are positioned substantially in the plane of the substrate. The substrate is then physically manipulated (e.g., folded, bent, corrugated, rotated, etc.) so that the setae become extended in an outwardly direction from the plane. Among other things, this provides a three-dimensional material having enhanced adhesive properties.

15 Claims, 15 Drawing Sheets

(56) References Cited

U.S. PATENT DOCUMENTS

| | | | |
|---|---|---|---|
| 6,872,439 | B2 | 3/2005 | Fearing et al. |
| 7,011,723 | B2 | 3/2006 | Full et al. |
| 7,229,685 | B2 | 6/2007 | Full et al. |
| 7,691,307 | B2 | 4/2010 | Fearing et al. |
| 7,691,760 | B2 | 4/2010 | Bergsten et al. |
| 7,709,087 | B2 | 5/2010 | Majidi et al. |
| 7,799,423 | B2 | 9/2010 | Majidi et al. |
| 7,811,272 | B2 | 10/2010 | Lindsay et al. |
| 7,828,982 | B2 | 11/2010 | Full et al. |
| 7,914,912 | B2 | 3/2011 | Fearing et al. |
| 2008/0070002 | A1 | 3/2008 | Majidi et al. |

OTHER PUBLICATIONS

Sitti et al., "Nanomolding Based Fabrication of Synthetic Gecko Foot-Hairs," MP2: Nanotechnology: biological systems and applications, IEEE-NANO 2002, Aug. 26, 2002, 4 pages.

Steinhart et al., "Polymer Nanotubes by Wetting of Ordered Porous Templates," Science, vol. 296, No. 5574, Jun. 14, 2002, p. 1997.

Tong et al., "Multiwalled Carbon Nanotube / Nanofiber Arrays as Conductive and Dry Adhesive Interface Materials," *Proceedings of the 3rd ASMS Integrated Nanosystems Conference—Design, Synthesis, and Applications*, Sep. 22-24, 2004, 7 pages.

Search Report and Written Opinion for PCT/IB2011/054297 dated May 30, 2012, 13 pages.

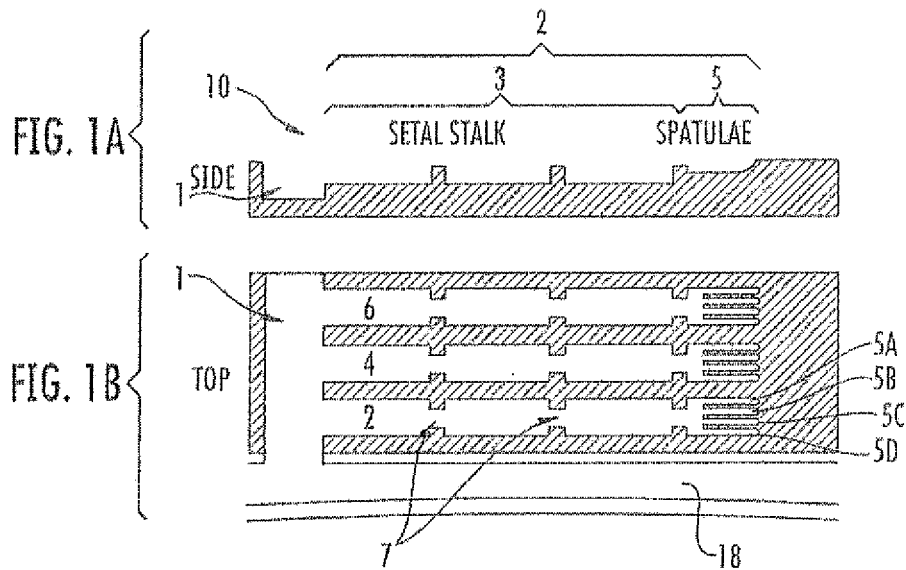
FIG. 1A
FIG. 1B
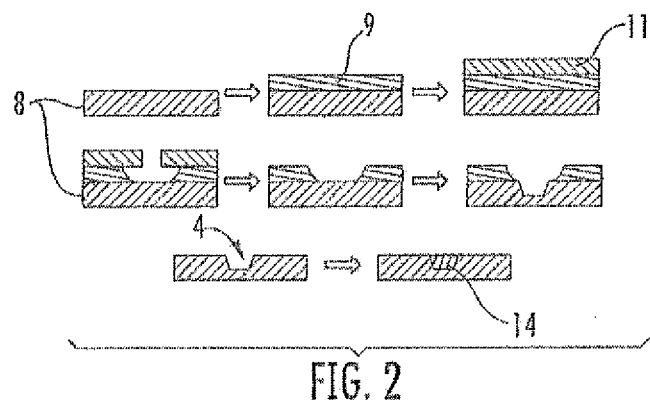
FIG. 2
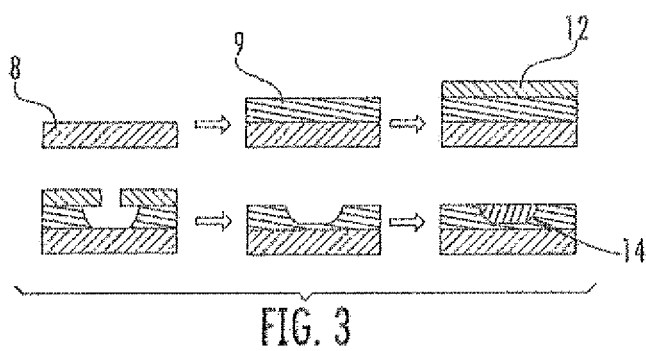
FIG. 3

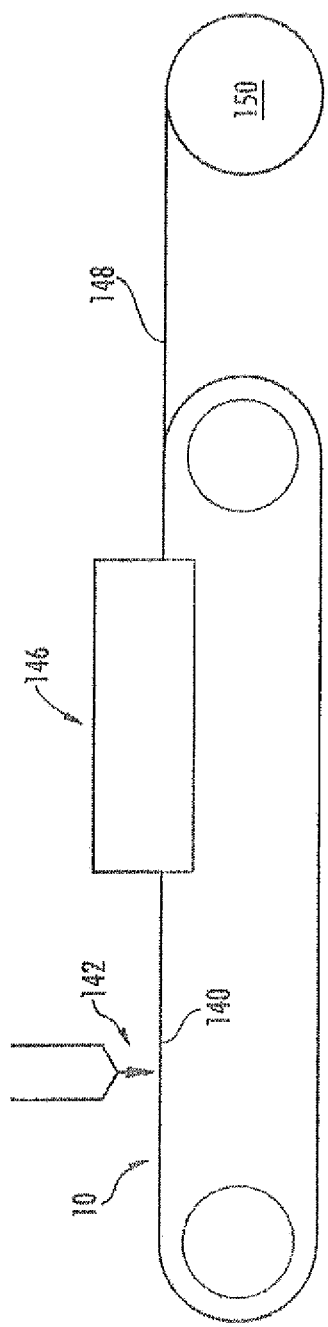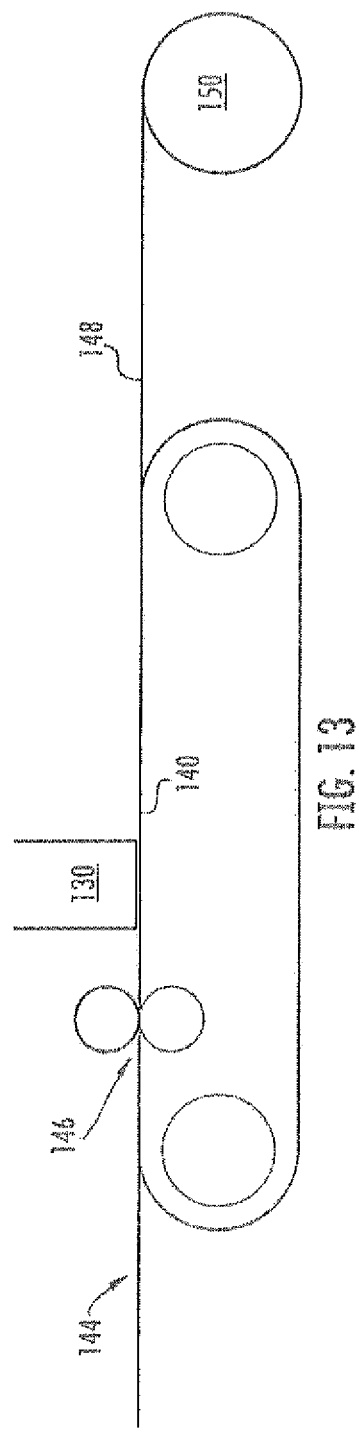

SYNTHETIC GECKO ADHESIVE ATTACHMENTS

BACKGROUND

The natural adhesive capability of the gecko foot allows the animal to adhere to surfaces of many types under most conditions. The adhesive capability is provided by numerous hair-type extensions, called setae, on the feet of the gecko. Gecko setae include stalks having diameters in the range of 5 micrometers. At the distal end, each stalk branches out into nano-sized spatulae, with roughly 100 to 1000 spatulae on each stalk, each of which is about 0.2 micrometers in length. Adhesion between the spatulae and a contacting surface is obtained due to van der Waals forces. The attractive forces between a single spatula and a surface can be on the order of 100 nanoNewtons (nN). The setae can be readily separated from the surface by the animal curling its toes off of the surface from the tips inward. This peeling action alters the angle of incidence between millions of individual spatulae and the surface, reducing the van der Waals forces and allowing the animal to move across the surface.

Multiple methods have been proposed for the formation of synthetic gecko setae. For instance, Full, et al. (U.S. Patent Application Publication No. 2004/0005454) describe several formation methods, including an etching process in which a recess is etched in a semiconductor substrate, nitride and oxide layers are deposited, the surface is patterned and etched, and the underlying substrate is etched, causing the oxide and nitride layers to curl away from the substrate and form a shaft structure. Another method of Full, et al. includes utilizing an excitation source to apply energy to a sensitive material. Upon application of the energy, the sensitive material exhibits a change in volume and the altered volume is selectively etched away, forming extending tubes. Other methods of Full, et al. include polymer etching, molding by use of a narrow glass tube, lithography methods utilizing electrostatic attraction to 'grow' a layer of protrusions on a substrate, and utilization of a nano-imprinting roller.

Fearing, et al. (U.S. Patent Application Publication No. 2003/0208888) describes a method for forming a microstructure including a stalk that supports a protrusion at an oblique angle relative to a supporting surface. The described method includes molding a structure having the desired shape, the structure is then removed to form a template, and the template is molded with a polymer. Other formation techniques have been described by Sitti, et al. (Nanomolding Based Fabrication of Synthetic Gecko Foot-Hairs, *Proceedings of the 2nd IEEE Conference on Nanotechnology*, 2002) including a first method in which an AFM tip is used to form dimples on a deformable surface, and a second method using a nano-pore membrane as a template.

Such 3-D molding processes have proven problematic due to the very high aspect ratio of the structures that are formed and must be removed from the mold. Formation of hierarchical structures that include both micro- and nano-sized portions has proven particularly challenging and typically requires multiple molding steps.

Substrates including arrays of synthetic gecko setae including hierarchical micro- and nano-sized portions and methods for forming such substrates would be useful in the art, for instance in development of fasteners for a variety of articles.

SUMMARY

In accordance with one embodiment of the present disclosure, an adhesive material is disclosed. The adhesive material comprises a first laterally extending support and a second laterally extending support that is adjacent to the first laterally extending support in a longitudinal direction. A first plurality of setae extend outwardly from the first support and a second plurality of setae extend outwardly from the second support. The setae contain a stalk and a spatula that extends from the stalk. The stalk has a length of from about 50 nanometers to about 500 micrometers and a width of from about 10 nanometers to about 50 micrometers, and the spatula has a length of from about 20 nanometers to about 20 micrometers and a width of from about 2 nanometers to about 1 micrometer. Further, the first and second laterally extending supports are either directly or indirectly connected to one another. For instance, the two laterally extending supports can be indirectly connected to one another via a connecting member that extends from the first laterally extending support to the second laterally extending support.

In accordance with one embodiment, the setae can include one or more hinges along the length, so as to define multiple degrees of freedom for the setae. For instance, a seta can be hinged at one or more of the base, at one or more locations along the stalk between the base and the spatula, at the top of the stalk, where the stalk meets the spatula, and on the spatula.

Also disclosed herein are disposable absorbent articles incorporating the adhesive material, for instance as a closure or an attachment device. For example, an attachment device can include a plurality of setae extending outwardly from first and second laterally extending supports. The two laterally extending supports can be adjacent to each other in a longitudinal direction and can be directly or indirectly connected to one another. The attachment device can also include a flexible base layer that can support the laterally extending supports. For instance, the laterally extending supports can be adhered to the flexible base layer or the flexible base layer can be a portion of a substrate that also defines the laterally extending supports.

Methods for forming the adhesive material are also disclosed. For instance, a method can include molding a planar polymeric substrate so as to define a first laterally extending support and a plurality of setae, and then aligning the first laterally extending support with a second laterally extending support. The second laterally extending support also defining a plurality of setae. Upon alignment, the setae will be rotated out of the plane of formation. In addition, the first and second laterally extending supports are adjacent to one another, are aligned in a longitudinal direction, and are directly or indirectly connected to one another. For instance, the two can be indirectly connected via a connection member that extends from the first support to the second support. In another embodiment, the first and second laterally extending supports can be formed separately and then aligned and directly connected to one another following formation.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1 illustrates a portion of a micromachined pattern mold for a linear fiber array including a side view (FIG. 1A) and a top view (FIG. 1B).

FIG. 2 schematically illustrates a silicon trench etching method.

FIG. 3 schematically illustrates a trench etching method utilizing a photoresist mask.

FIG. 12 illustrates a continuous molding process for forming a planar substrate defining linear arrays of synthetic setae.

FIG. 13 illustrates another molding process for forming a planar substrate defining linear arrays of synthetic setae.

Figure 4A:
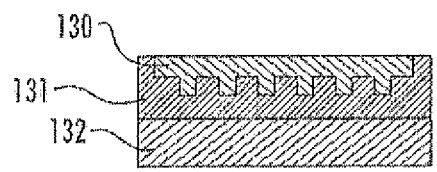
FIGS. 4A-4C schematically illustrate a nanoimprinting method.

Repeat use of reference characters in the present specification and drawings is intended to represent the same or analogous features of elements of the disclosed subject matter. Other objects, features and aspects of the subject matter are disclosed in or are obvious from the following detailed description.

DETAILED DESCRIPTION

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

Generally speaking, the present invention is directed to an adhesive material that contains a plurality of setae that include a stalk and spatula extending therefrom. To form the adhesive material, a substantially planar substrate may be initially molded to define the setae. In this initial configuration, the setae are positioned substantially in the plane of the substrate. The substrate is then manipulated (e.g., rotated, folded, bent, corrugated, etc.) so that the setae become extended in an outwardly direction from the plane of formation. Among other things, this provides a three-dimensional material having enhanced adhesive properties. Beneficially, the formation process can be a relative simple and inexpensive two step process including a first molding step of a planar substrate followed by a manipulation process to extend the synthetic setae from the plane.

A variety of different fabrication techniques may be employed to initially form the planar substrate that defines setae. For instance, surface micro-machining of molded substrates may be used in conjunction with lithographic masks to define the stalk and spatulae of each seta. FIG. 1 illustrates one embodiment of a surface micromachined pattern mold 10 including a side view (FIG. 1A) and a top view (FIG. 1B). The mold 10 defines a laterally extending support 1 from which an array of individual trenches 2, 4, 6 can extend. The depth of the mold 10 at the laterally extending support 1 can be greater than other portions of the mold (FIG. 1A) so as to form a supportive base for the setae. The laterally extending support 1 can extend across the width of the mold (FIG. 1B). Adjacent to the array, a mold 10 can define a support section 18. As can be seen, the laterally extending support section 1 is contiguous with the support section 18.

A trench 2 can include a stalk portion 3 and spatula portion 5. Trench depth and cross sectional width and shape can determine the stalk and spatula diameter and shape of the formed setae, and trench length can control the ultimate length of the formed setae. Depth and cross sectional width can vary along the length of a trench. For instance, a stalk portion 3 can form a stalk having a width of from about 10 nanometers to about 50 micrometers, in some embodiments from about 20 nanometers to about 15 micrometers, and in some embodiments, from about 1 micrometer to about 10 micrometers (e.g., about 5 micrometers). The stalk portion 3 can be the same shape along the entire length or can vary. In the illustrated embodiment, the stalk portion 3 includes narrower segments 7 that can form hinged joints in the formed setae. The narrower segments can provide hinges that can increase number of degrees of freedom of a seta. Wider portions (not shown) could likewise be defined in a stalk portion 3.

A stalk portion 3 can generally have a length of from about 50 nanometers to about 500 micrometers, in some embodiments from about 1 micrometer to about 300 micrometers, and in some embodiments, from about 10 micrometers to about 150 micrometers (e.g., about 100 micrometers). Center to center spacing between adjacent seta in an array can depend upon the cross sectional dimension of each seta, but in general can be from about 100 nanometers to about 500 micrometers, and in some embodiments, from about 1 micrometer to about 100 micrometers, or from about 2 to about 30 micrometers (e.g., about 10 micrometers).

The terminal portion 5 of a trench 2 can define spatulae formed by trenches 5A, 5B, 5C, 5D on the mold 10. Each spatula trench 5A, 5B, etc. can be formed so as to form a spatula having a width of from about 2 nanometers to about 1 micrometer, and in some embodiments from about 10 nanometers to about 500 nanometers, for instance from about 20 nanometers to about 300 nanometers in a cross-sectional dimension. A spatulae portion 5 can define multiple trenches, each forming a single spatula having a length of from about 20 nanometers to about 20 micrometers, in some embodiments from about 50 nanometers to about 15 micrometers, and in some embodiments, from about 1 micrometer to about 10 micrometers (e.g., about 5 micrometers). By way of example, a spatulae portion can define from about 3 to about 2500 individual trenches, each of which can form an individual spatula. In some embodiments, a spatulae portion can define from about 5 to about 500 trenches, for instance from about 5 to about 100 trenches (e.g., about 25 trenches).

A branch 5A can define a single cross sectional shape along the entire length, as shown, or alternatively can include variation along the length. For instance, nano-imprinting can be used to add an additional level of hierarchy to each branch 5A, 5B, etc., such as a flat end portion, an additional formation at the distal end of a branch, a variation in cross section along the length, and so forth. A branch can optionally include one or more hinges (not shown). Additional variation in the cross section of individual spatula portions can translate to an increase in the area of contact between the formed setae and a surface, which can increase adhesion strength.

The mold 10 can be formed according to any known micromachining method. For instance, the mold can be formed using etching and masking techniques as are generally known in the art. FIG. 2 illustrates one mold formation method encompassed herein. In this embodiment, a substrate 8, e.g., a silicon based substrate such as a single crystal silicon wafer, can be utilized as a structural layer. A nitride layer 9, e.g., an Si-nitride layer, can be formed as an etch-stop and/or as a protection layer for any underlying structures formed in the substrate 8. An oxide layer 11, e.g., an Si-oxide, can be applied as a sacrificial layer. The nitride and oxide layers can be formed via standard methods, such as chemical vapor deposition (CVD) processes as are generally known in the art. The layers 9, 11 can then be selectively etched, for instance by the use of hydrofluoric acid (HF). The most widespread method of HF-based etching is wet etching in a mixture of HF and water, though it should be understood that HF wet etching is not a requirement in the present disclosure, and any suitable etching method may be utilized. Following a first etch and removal of the sacrificial layer 11, a second etch may be carried out, to form a trench 4 in the substrate 8, as shown. For molding, the trench 4 can be filled with a polymeric material 14.

In another embodiment, illustrated in FIG. 3, an etch can be carried out utilizing a photoresist mask. According to this method, a layer 12 of photoresist (PR) material can be formed (e.g., via spin-coating) on the surface of a nitride layer 9. The resist layer 12 can then be selectively exposed to radiation such as ultraviolet light, electrons, or x-rays. After exposure, the PR layer 12 can be subjected to development, which destroys unwanted areas of the PR layer 12, exposing the corresponding areas of the underlying layer. The areas with no resist material left on top of them can then be subjected to subtractive processes, allowing the selective removal of material on the underlying layer 9, as shown.

Figure 4B:
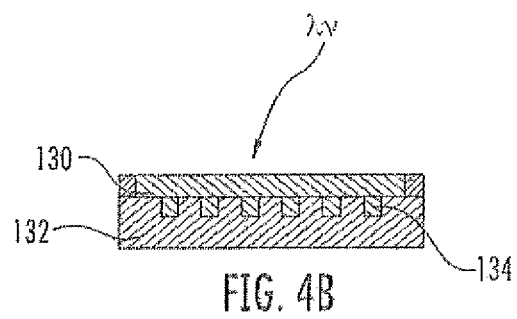
Figure 4C:
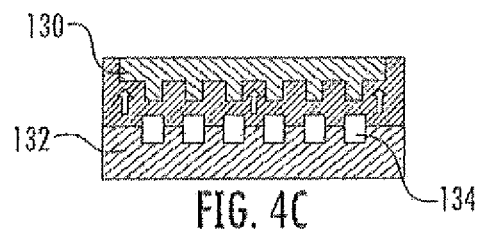

A method for molding nano-sized structures such as nanoimprint lithography methods can be utilized in forming setae, for instance in forming additional hierarchical structure on each individual spatula. Nanoimprint lithography is a nano-scale lithography technique in which a hybrid mold is utilized that acts as both a nanoimprint lithography mold and a photolithography mask. A schematic of a nanoimprint lithography technique is illustrated in FIGS. 4A-4C. During fabrication, a hybrid mold 130 can imprint into a substrate 132 via applied pressure to form features (e.g., flat end portions of a spatula) on a resist layer 131 (FIG. 4A). In general, the surface of the substrate 132 may be heated prior to engagement with the mold 130 to a temperature above its glass transition temperature ($T_g$). While the hybrid mold 130 is engaged with the substrate 132, a flow of viscous polymer may be forced into the mold cavities to form features 134 (FIG. 4B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 130 is then removed from the cooled substrate 132 at a temperature below $T_g$ of the substrate and polymer (FIG. 4C).

To facilitate the release of the nanoimprinted substrate 132 including fabricated features 134 from the mold 130, as depicted in FIG. 4C, it may be advantageous to treat the mold 130 with a low energy coating and reduce adhesion with the substrate 132, as a lower surface energy of the mold 130 and the resulting greater surface energy difference between the mold 130, substrate 132, and polymer may ease the release between the materials. By way of example, a silicon mold coating may be used such as trideca-(1,1,2,2-tetrahydro)-octytrichloro silane ($F_{13}$-TCS).

A nanoimprinting process is dynamic and can include filling a mold followed by detachment of a formed polymer from the mold. To fill the mold features, the polymer temperature is typically raised to a level high enough to initiate flow under the applied pressure. The higher the temperature, the lower the polymer viscosity, and the faster and easier the mold will fill. A higher pressure will also improve the fill rate and overall fill for better mold replication. To release the nanoimprinted substrate from the mold, the substrate temperature may be lowered to a point where the yield strength exceeds the adhesional forces exerted by the mold. A mold 10 can be filled with polymer using any of a variety of techniques such as molding of thermoplastic film or casing of Liquid thermosets. Techniques such as spin-coating, thin film deposition, or thermal injection molding can also be used to fill a mold with desired polymeric materials.

As mentioned, a formation process can be a relatively simple process including molding of a substantially planar substrate followed by manipulation of the formed substrate. In carrying out the molding step of the procedure, the mold can be filled with any suitable polymeric material including one or more hydrophobic or hydrophilic polymers. Useful polymers can include natural, synthetic, and semi-synthetic polymers, copolymers, or blends thereof. In one embodiment, an auxetic material (i.e., a material that has a negative Poisson's ratio) can be used. Exemplary polymeric materials can include keratin (e.g., β-keratin or other keratin materials and derivatives, such as those obtained from wool), polyesters, polyolefins, polyamides, polyurethanes, and silicone materials. Exemplary silicone materials can include polydimethysiloxane and its derivatives and copolymers, such as diphenylsiloxane-dimethylsiloxane copolymer (Catalog No. PMM-5021 of Gelest, Inc., Morrisville, Pa.), or polydimethylsiloxane aminoalkyl copolymers. The polymeric materials may also include any of a variety of known additives, such as nucleating agents, dyes, anti-static agents, antioxidant agents, antimicrobial agents, adhesion agents, stabilizers, plasticizers, brightening compounds, clarifying agents, ultraviolet light stabilizing agents, surface active agents, odor enhancing or preventative agents, light scattering agents, halogen scavengers, and so forth. In addition, additives can be included in the polymeric materials to be molded, e.g., in the melt, or can be applied as a surface treatment the molded polymeric material.

Figure 5:
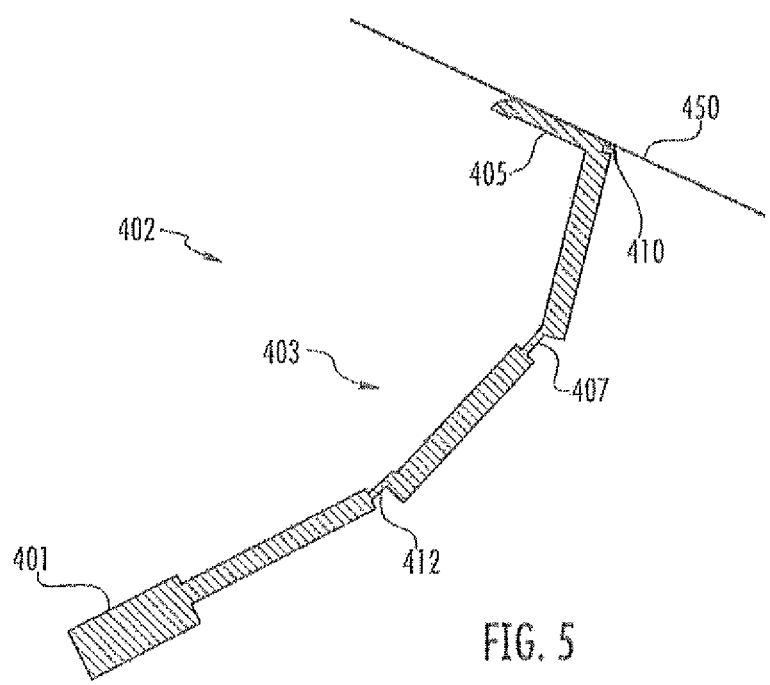
FIG. 5 illustrates a single seta following molding, the stalk including two hinges along the stalk length and a hinge between the stalk and the spatula.

FIG. 5 schematically illustrates a single seta 402 extending from the laterally extending support 401 following formation and removal from a mold. The stalk 403 includes three flexure joints, or hinges, 407, 410, 412 as shown. The inclusion of one or more hinges in a stalk can improve the adhesion characteristics of the seta. For instance, the inclusion of one or more hinges in a seta can increase the degrees of freedom of the extended seta and can improve contact between the surface of the seta and a contacting material, thereby improving adhesion characteristics between the two. For example, as illustrated in FIG. 5, when the seta 402 is pushed up against a contacting surface 450, the hinges 410, 407, 412, can flex, leading to contact between the spatulae 405 and the contacting surface 450. The presence of the hinges can allow for increase in the surface area of contact between the spatulae 405 and the contacting surface 450, which can increase the attractive force between the two.

The number of hinges formed on a single seta can vary. By way of example, a single seta can include up to about 10 hinges. For instance, in one embodiment, a seta can have no joints formed along the length of the seta, and the motion of the seta will be primarily defined by the flexibility of the material forming the seta, with no additional degrees for freedom provided in the length of the seta. Alternatively, a seta can include 1, 2, 3, or more hinges spaced along the length of the seta.

Figure 6:
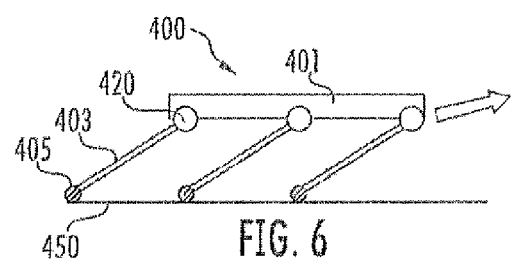
FIG. 6 illustrates an array of three setae, each including a hinge at the base of the setae.

FIG. 6 illustrates an array of three setae including a stalk 403 and a spatula 405. In this embodiment, each seta includes a single hinge 420 at the base of the stalk 403 where the stalk 403 meets the laterally extending support 401. In this embodiment, the stalk can exhibit a wider degree of motion when the array 400 is displaced as designated by the arrow as compared to a stalk that does not include a hinge at the base. In addition, the inclusion of the single hinge 420 at the base of the stalk can increase the surface area of contact between the spatulae 405 and the contacting surface, but, as the stalk itself is not hinged, this increase may not be extremely large. Upon application of force in a direction as signified by the arrow, the array 400 can adhere to the contacting surface 450.

Figure 7A:
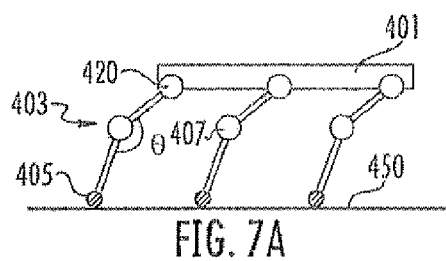
FIGS. 7A-7B illustrate an array of three setae, each including two hinges, one at the base, and one along the stalk, and illustrating displacement of the setae with the setae in a first conformation with the adhering material.
Figure 7B:
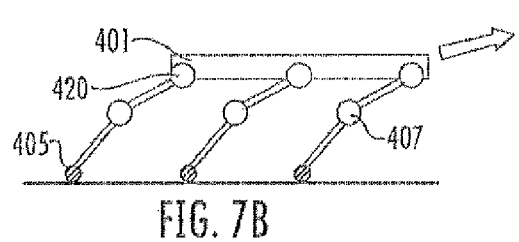

FIGS. 7A and 7B illustrate an array of three setae that, in addition to a hinge 420 at the base between the stalk 403 and the laterally extending support 401, also includes a hinge 407 along the length of the stalk. In this particular embodiment, the hinge 407 is angled toward the material, i.e., the angle θ is less than 180°, and upon application of force as illustrated by the arrow, the spatula 405 can adhere to the material 450.

The addition of a second hinge 407 can further improve the surface area of contact between the spatulae 405 and the contacting surface 450. In addition, due to the added degrees of freedom of the stalk brought about by the hinges 407, 420, the spatula 405 can become separated from the adhering material 450 without fracture of the tip, meaning that the setae array can be utilized multiple times as a reusable adhesive material.

Figure 8A:
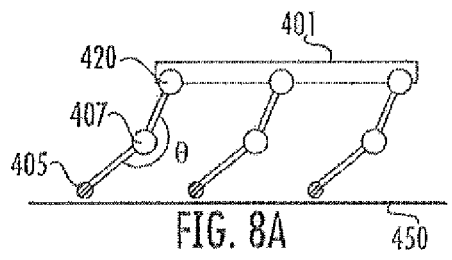
FIGS. 8A-8B illustrate the array of three setae of FIG. 7, illustrating the displacement of the tip when the setae are in a second conformation with the adhering material.
Figure 8B:
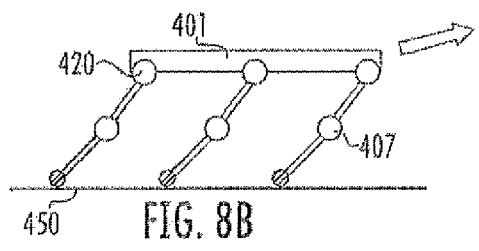
Figure 9A:
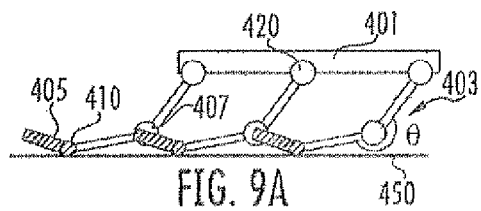
FIGS. 9A-9B illustrate an array of three setae, each including three hinges, one at the base, one along the stalk, and one between the stalk and the spatula, and illustrating contact leading to adherence of the setae with the setae in a first conformation with the adhering material.
Figure 9B:
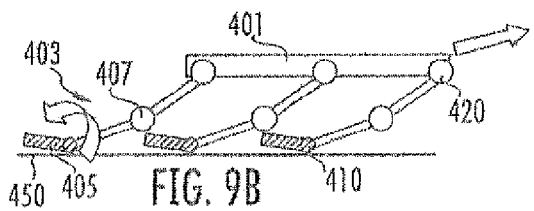

In the embodiment of FIGS. 8A and 8B, the array of three setae is similar to that of FIGS. 7A and 7B, but in this case, the angle θ of the hinge 407 is greater than 180°, leading to a different conformation between the stalk 403 and the adhering material 450. No matter what the conformation of the angle formed at hinge 407, however, the seta can remain in good contact with the contacting surface 450. In other words, the array can withstand forces applied in various directions without separation between the array 400 and the contacting surface 450, because the hinges 407, 420 can rotate and absorb a portion of the applied force. Thus, the inclusion of hinges 420, 407 can improve the adherence between the array 400 and the contacting surface 450 even when shearing forces are applied to the system.

Figure 10A:
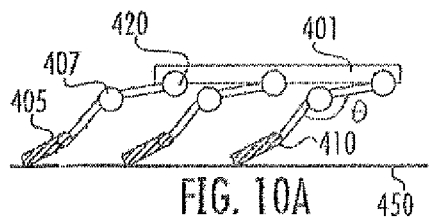
FIGS. 10A-10B illustrate the array of three setae of FIG. 9, illustrating the contact leading to adherence of the setae with the setae in a second conformation with the adhering material.
Figure 10B:
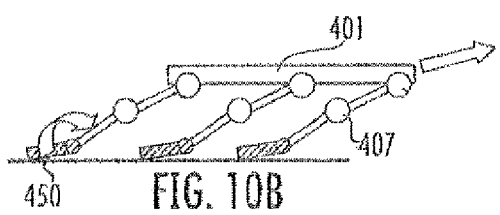

FIGS. 9A-9B and 10A-10B illustrate an example of an array of three setae in which each seta 403, includes three hinges. Hinge 420 is at the base of the stalk, hinge 407 is along the length of the stalk, and hinge 410 is at the top of the stalk, where the stalk meets the spatula 405. As shown by the arrows, whether the stalk hinge 407 is at an angle θ of greater than 180° (as in FIGS. 9A-9B) or less than 180° (as in FIGS. 10A-10B), upon application of force as illustrated by the arrow, the spatula 405 can obtain good contact with the contacting surface 450 over the surface area of the spatulae 405. For instance, in the embodiment illustrated in FIGS. 9A and 9B, the spatula 405 can contact the surface 450 with a 'heel' first conformation, and upon further application of shearing force, the remainder of the spatula 405 can contact the surface 450, leading to the adherence of the spatula 405 to the surface 450. In the embodiment of FIGS. 10A and 10B, the altered conformation of the stalk leads to a 'toe' first conformation of the spatula. However, upon additional force application, the remainder of the spatula 405 is forced in to contact with the surface 450 and the setae become adhered to the surface 450. The addition of the third hinge 410 at the distal end of the stalk can further improve the degrees of freedom of motion of the seta, which can improve adhesion through both the increase in surface area of contact and the ability to withstand shearing forces.

Figure 11:
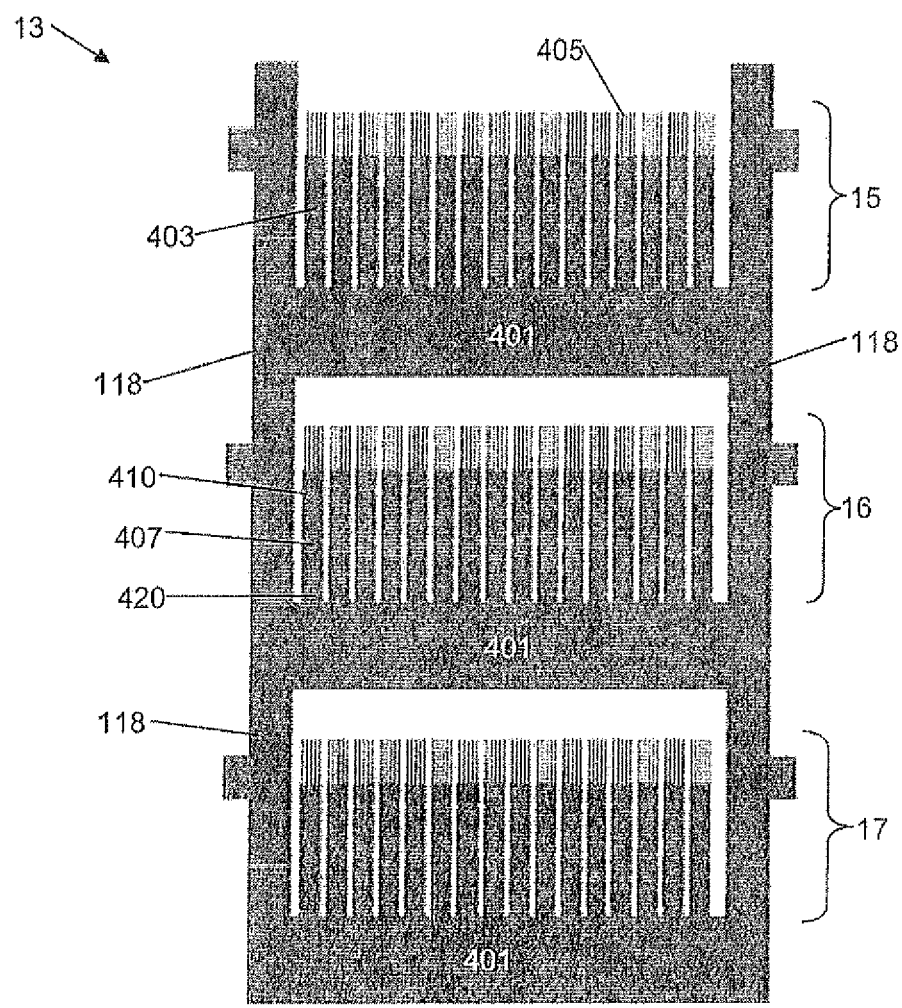
FIG. 11 illustrates a planar substrate including three substantially planar molded linear arrays of synthetic setae including hierarchical micro- and nano-sized features.

As discussed, a molded substrate can be initially formed in a planar configuration and then manipulated to cause the setae to extend outwardly. FIG. 11 illustrates a substantially planar molded polymeric substrate 13 following removal from a mold. Mechanical peeling may be used to separate the substrate 13 from the substrate mold. Standard techniques for improving mold release such as smooth conformal coatings, sacrificial layers, and low surface energy coatings can be utilized if desired to improve successful removal.

In this particular embodiment, substantially planar substrate 13 includes three linear arrays of setae 15, 16, and 17 that are connected to one another at support section 118 at the end of each array and include a laterally extending support 401 across the width of each array 15, 16, 17. There is no particular limit as to the size of any single array (e.g., number of individual seta or support sections across an array) or the number of linear arrays formed in a single substrate. For instance, a continuous formation process can be utilized to form a continuous substrate of linear arrays, and each array can be of any desired width and include a plurality of synthetic setae. Each seta of a linear array can include hinges 410, 407, 420 on each stalk 403. At the distal end of each stalk 403 are a plurality of spatulae 405.

FIG. 12 illustrates one particular molding method for forming a continuous planar substrate that defines linear arrays of synthetic setae. According to this method, the mold 10 can be on the surface of an endless travelling belt 140. The belt 140 can include only the mold structure (e.g., a single crystal silicon structural layer defining the trenches of the mold) or alternatively one or more support layers. For example, the belt 140 can be a laminate structure including support layers as are generally known in the art and these support layers can be beneath an upper layer that carries or defines mold 10. The mold 10 can be filled with a polymeric material, as at 142. Filling can take place via any suitable means, generally depending upon the nature of the polymeric material and the specific molding process. For example, a polymeric material can be a thermoplastic melt or a low viscosity thermoset composition and the filling process can be an extrusion process as is known in the art. Thereafter, the belt 140 can carry the filled mold 10 to a station 146 where the polymeric material can be cured. For instance, station 146 can include a furnace that can heat and cure the polymeric material held in the mold 10. Any curing method may be utilized including temperature curing, radiation curing, air drying, and so forth. In one embodiment, the polymeric material can be cured by use of electromagnetic radiation, e.g., UV radiation.

In another formation method, illustrated in FIG. 13, a precursor substrate 144 can be fed to belt 140. The precursor substrate can be, for instance, a hybrid mold substrate as may be utilized in a nanoimprint lithography process. During fabrication, a hybrid mold 130 can imprint into substrate 144 via applied pressure to form features on a resist layer of the precursor substrate 144. The surface of the substrate 144 may be heated, for instance by use of a heated nip 146, prior to engagement with the mold 130. The hybrid mold 130 can be engaged with the substrate 144 to shape the substrate 144 as desired while a flow of viscous polymeric material may be forced into the shaped mold cavities to form the features of the synthetic setae. In this embodiment, the resist layer can be exposed to UV radiation while the hybrid mold is engaged with the substrate. Following formation, a planar substrate 148 that defines the synthetic setae in the plane of the substrate can be collected for further processing, such as on take up reel 150. Alternatively, the substrate 148 can proceed to further processing on a single processing line, which can include folding the setae out of the plane of substrate 148 to form a three dimensional material.

Following a molding process, the planar substrate such as that illustrated in FIG. 11 may be manipulated so that the setae are rotated to extend out of the substrate plane. A variety of different techniques may generally be employed for this purpose, including folding, bending, corrugating, rotating, etc., all or a portion of the substrate.

Figure 14:
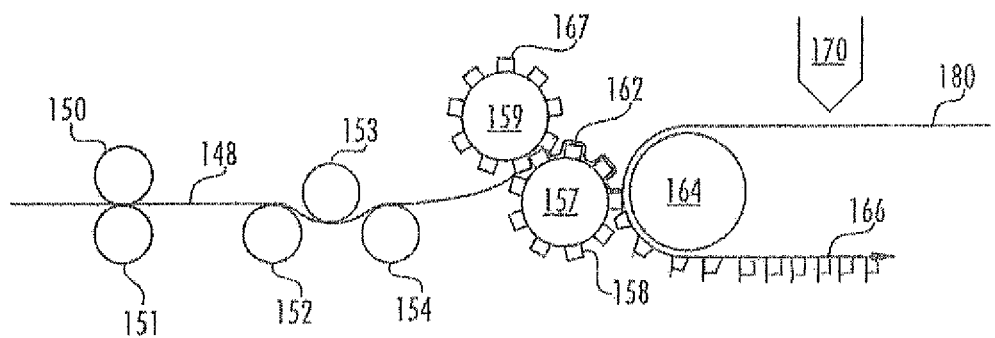
FIG. 14 illustrates a corrugation process as may be used to fold the synthetic setae out of the plane of the molded substrate and adhere the three dimensional material to a backing sheet.

Referring to FIG. 14, one particular embodiment is illustrated in which a planar substrate 148 that defines a plurality of arrays is corrugated so as to manipulate the substrate and to rotate and extend the setae outwardly from the plane of formation. As shown, a pair of drive rolls 150, 151 can feed the substrate 148 at a predetermined rate to tensioning rolls 152, 153 and 154, and then into a corrugation section. The corrugation section can include a substantially cylindrical corrugation drum 157 having a multiplicity of substantially uniform parallel, longitudinally extending grooves 158 formed in the surface of the drum and a cooperating corrugation drum 159 having longitudinally extending teeth 167 for pressing the substrate 148 into the grooves 158 so as to corrugate the substrate 148. More specifically, the substrate 148 can be aligned with the drum 157 such that the linear arrays of synthetic setae will align with the extending grooves of the drum 157. As the substrate 148 passes through the interlocking nip formed between grooves 158 and teeth 167, the substrate can be corrugated so that the setae extend out of the plane of the as-formed substrate.

If desired, the now three dimensional material 162 can be adhered to an optional backing sheet 180 to improve the stability of the three dimensional material 162 and prepare the material for further processing, e.g., attachment to a device as a closure. Of course, adherence of a three dimensional material to a backing sheet is not a requirement of the present disclosure. The backing sheet 180 can be any suitable material, with preferred materials generally depending upon the desired application of the three dimensional material. For example, a backing sheet 180 can comprise a single layer or multiple layers of material. It can be a film, an apertured film, a fibrous web, a liquid pervious web such as a meltblown web, an activated carbon fabric, and the like, or a composite structure comprising one or more such materials. The thickness of the backing sheet 180 may be uniform or non-uniform, and may have a repeating pattern (not shown) of thickness variations such as a rectangular grid or series of lines having 10% or greater thickness than the mean thickness of the backing sheet. The backing sheet 180 may be a film or web that has been creped, embossed, apertured, coated on one or both sides with a hydrophobic or hydrophilic agent or a metal oxide such as titanium dioxide, treated with a UV absorbing material, thermally treated to cause shrinkage, and the like.

The backing sheet 180 can also be bonded to the three dimensional material 162 according to any method including, without limitation, thermal bonding, ultrasonic bonding, use of an adhesive, and the like. For example, an adhesive can be utilized to bond the three dimensional material 162 to the backing sheet 180. According to this embodiment, the backing sheet 180 can pass under an adhesive applicator 170, shown here in the form of a nozzle, where adhesive is applied. It will be understood that the adhesive may be applied in a continuous bead or in an interrupted but substantially regular pattern, for instance a pattern of dots, lines, and so forth. Alternatively, the adhesive can be applied by a roll type applicator in either a continuous or intermittent fashion such as by a print roll. In one embodiment, an adhesive can be applied in a pattern to coincide with the folding pattern of the three dimensional material 162, such that little or no adhesive is applied in those areas where the setae extend out from the plane of the as-formed, planar substrate.

The backing sheet 180 and the three dimensional material 162 can be adhered to one another between an anvil roll 164 and the corrugation drum 157 to form a three dimensional laminate 166. To transfer the material 162 to the backing sheet 180 a vacuum can be drawn within the anvil roll 164, as is generally known in the art.

Figure 15:
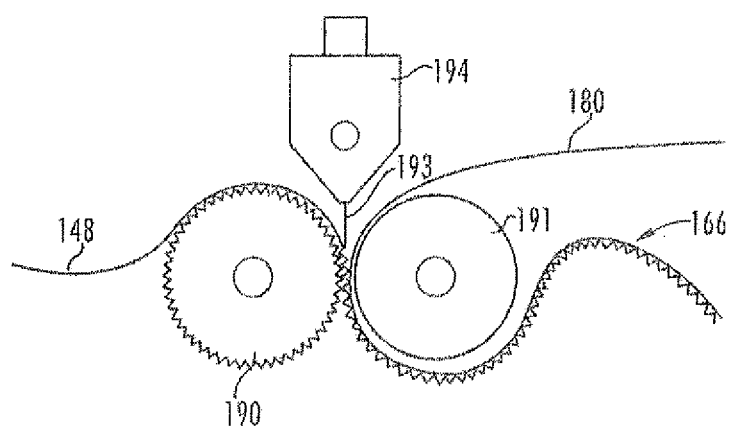
FIG. 15 illustrates another corrugation process as may be used to fold the synthetic setae out of the plane of the molded substrate and adhere the three dimensional material to a backing sheet.

Another corrugation method that may be employed is illustrated in FIG. 15. In this embodiment, a two-roll process is employed rather than a three-roll process as described above. More particularly, this method employs first and second corrugation drums 190 and 191. The corrugation drum 191 has a generally flat surface, while the corrugating drum 190 defines a recessed pattern that can be geared to or driven by corrugation drum 191 so that the two move in opposite rotational directions at the same circumferential speed. The planar molded substrate 148 can be carried over the surface of the corrugation drum 190 and into the nip formed between the corrugation drums 190 and 191. An adhesive 193 can be extruded from a die 194 into the nip while simultaneously supplying a backing sheet 180 along the surface of the second corrugation drum 191. This results in an extruded adhesive layer being deposited between the backing sheet 180 and the substrate 148 that bonds the backing sheet 180 and the substrate 148. The three dimensional laminate 166 can then be carried partially around the corrugation drum 191 to complete cooling.

An adhesive material including a plurality of synthetic setae can be formed through a relatively simple two-step molding and manipulation process as disclosed. Following manipulation, the as-formed, substantially planar substrate can take on a new, non-planar cross section. The cross-sectional geometry of the manipulated, e.g., folded, substrate can have any desired shape and complexity and can include the synthetic setae extending therefrom. For example, FIGS. 16A-16E illustrate non-limiting examples of different folding schemes for a substrate.

Figure 16A:
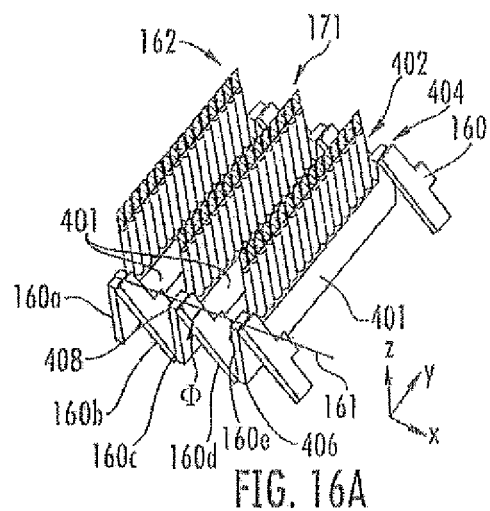
FIGS. 16A-16E illustrate various three dimensional materials following a corrugation process.

With reference to the coordinate system illustrated in FIG. 16A, a planar substrate such as is illustrated in FIG. 11 has a longitudinal direction along the x-coordinate and a lateral direction along the y-coordinate. Following folding, the setae 402 attached to laterally extending support 401 extend upward along the z-coordinate. Note, however, that the longitudinal direction of the substrate remains the same after folding, i.e., the folded substrate 162 has a longitudinal direction along the x-coordinate in the embodiment of FIG. 16A.

As can be seen, the substrate 162 includes laterally extending supports 401 that are spaced apart from each other, as shown. Each laterally extending support 401 includes lateral edges 160a, 160c, 160e. Extending from a first laterally extending support to a second laterally extending support is a connection member 160b, 160d. Though illustrated as present on only the external edges of the substrate 162, it should be understood that a substrate can include connection members at multiple intervals across the width of the substrate in the lateral direction. As can be seen, upon folding, several folds 404, 406, 408 can be formed in the substrate such that a fold or a fold line (e.g., 408) defines the location from which a connection member (160d) extends from a laterally extending support including lateral edge 160c.

In the embodiment of FIG. 16A, the connection members 160b, 160d, extend in a substantially straight line between the lateral edge of a first laterally extending support and the lateral edge of an adjacent laterally extending support, as shown. In addition, connection member 160d forms an angle Φ relative to the longitudinal direction 161 of the substrate 162.

Figure 16B:
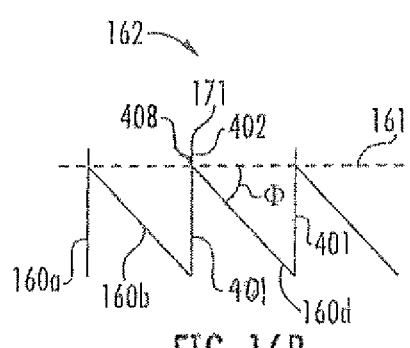

FIG. 16B illustrates a side view of the array 162 of FIG. 16A. This view may more clearly illustrate the angle Φ between the longitudinal direction 161 of the substrate 162 and the connection member 160d that extends between two adjacent laterally extending supports 401.

Figure 16C:
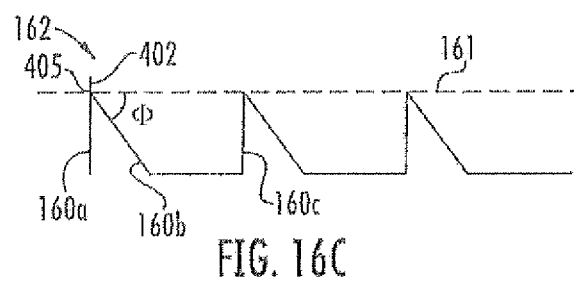

As mentioned, the cross sectional shape of a three dimensional substrate following folding can vary. Accordingly, either or both of the laterally extending supports and the connection members of a substrate can be folded in the longitudinal and/or lateral directions. For instance, FIG. 16C illustrates another embodiment of a three dimensional material 162. In this embodiment, connection member 160b is folded. More specifically, a portion of connection member 160b lies at an angle Φ relative to the longitudinal direction 161 of the substrate 162, as shown, while a second portion extends in the longitudinal direction 161. A fold in connection member 160b such that a portion of the connection member lies in the longitudinal direction can improve adhesion of the three dimensional substrate 162 to a second material, as it can increase the surface area available for adhesion.

Figure 16D:
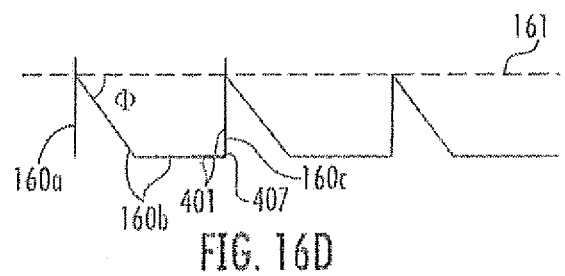

The three dimensional material of FIG. 16D includes a fold in connection member 160b such that a portion of the connection member is at an angle Φ to the longitudinal direction 161 and a portion lies along the longitudinal direction, as in the embodiment of FIG. 16C. In addition, however, the substrate 162 includes a fold 407 that extends along a laterally extending support 401 of the substrate 162. In FIG. 16D, the bent edge of laterally extending support 401 has been exaggerated for clarity. Accordingly, a first portion of laterally extending support 401 lays in the x, y plane and a second portion of laterally extending support 401, on the other side of fold 407, extends in the z direction. Such an embodiment can further increase the surface area of the three dimensional material that remains in the original plane of the pre-folded substrate (i.e., the x, y plane of the illustrated coordinate system).

Figure 16E:
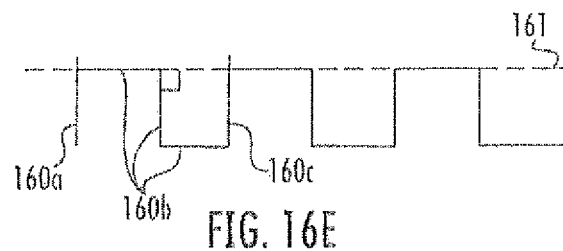

FIG. 16E illustrates yet another embodiment. In this embodiment, a connection member 160b has been folded into three portions, such that the cross sectional shape of the substrate is squared. In this embodiment, the angle Φ between the longitudinal direction of the substrate 161 and the portion of the connection member 160b is approximately 90°, with the other two portions of the connection member 160b being in the longitudinal direction, as shown.

Other folding schemes would be obvious to one of ordinary skill in the art. For instance, a portion of a connection member could be folded back, such that the angle Φ, as shown in FIGS. 16A-16E, is greater than 90°. Of course, in such an embodiment, the angle could be measured on the other side of the connection member. Thus, an angle Φ between the longitudinal direction of a substrate and a portion (or all) of a connection member can be up to 90°, depending on which side of the connection member the angle is measured on. In general, the angle Φ can be between about 10° and 90°.

Of course, the presented folding schemes are only a representation of schemes encompassed herein. Any other manipulation design in which a substantially planar substrate is manipulated so as to extend the synthetic setae of the substrate out of the plane is encompassed herein. For example, a laterally extending support can be straight in the lateral direction, as shown in FIGS. 16A-16E, or can define curvature.

In another embodiment, a planar substrate can be formed that includes only a single linear array. Following molding, this array can be either directly or indirectly connected to one or more additional arrays to form an adhesive material. More specifically, a linear array can be removed from a mold, rotated from the plane of molding, aligned with one or more additional rotated, planar arrays, and these arrays can be directly or indirectly connected to one another to form an adhesive material that includes a large number of setae.

Figure 17A:
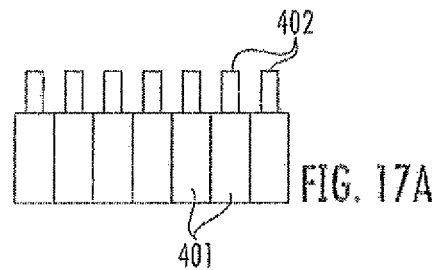
FIG. 17A illustrates individually formed linear arrays of synthetic setae directly connected to one another.

FIG. 17A illustrates an embodiment including a plurality of individually formed linear arrays including laterally extending supports 401 and setae 402 attached thereto. In FIG. 17A the lateral direction of the laterally extending supports 401 is perpendicular to the plane of the figure. Thus, the end edge of the laterally extending supports 401 and only a single seta 402 on each support is visible, as the other setae of the linear arrays are aligned behind the visible seta 402. In this embodiment, adjacent laterally extending supports are in direct contact with one another, with no connecting member there between. The arrays can be adhered directly to one another in a stacked arrangement as shown in FIG. 17A in those embodiments in which the laterally extending supports 401 are wide enough so as to maintain a distance between the adjacent arrays of setae.

Figure 17B:
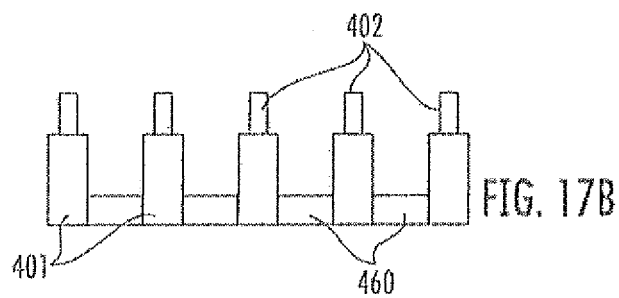
FIG. 17B illustrates individually formed linear arrays of synthetic setae indirectly connected to one another via a connecting member.

In another embodiment, illustrated in FIG. 17B, a connecting member 460 can be located between adjacent laterally extending supports 401. The connecting member 460 can extend the length of the laterally extending supports 401 or can be intermittently located along the laterally extending supports 401 in the lateral direction. A stacked arrangement of individually formed, rotated arrays can be directly or indirectly bonded to one another via any suitable means including, without limitation, use of adhesives, heat bonding, pressure bonding, welding, or combinations thereof.

A substrate including a plurality of linear arrays can provide a large number of spatulae for adhesion. For instance, a 10 mm wide substrate can include linear arrays each formed with 5000 setae across the width. A 100 mm long strip of this substrate including 1000 linear arrays can be folded with center to center spacing between each array of from about 5 μm to about 500 μm, for instance from about 5 μm to about 100 μm, or about 10 μm, thus providing $5\times10^6$ setae per square centimeter. Assuming each seta includes 400 spatulae, this would provide 2 billion spatulae per square centimeter. Assuming each seta includes 20 spatulae, this would provide 100 million spatulae per square centimeter.

The adhesive characteristics of a substrate can be generally linear with the number of spatulae. Thus, at about 50 nN attractive force per spatula, a seta including 20 spatulae can exhibit an attractive force of about 1 μN, and one square centimeter of the adhesive material as described above could provide a normal adhesion strength of about 5 N per square centimeter.

A substrate including a plurality of setae extending from a surface can be incorporated in a variety of products. In one embodiment, a substrate can be adapted as a fastener for an article, for instance in fastening an article to itself, as a closure, or in fastening an article to another article. By way of example, a substrate may be used as an attachment means for closing a disposable absorbent article around the torso of a wearer, or as attachment means for joining an absorbent article to another article such as an article of clothing, or as a body adhesive for joining a portion of an absorbent article to the skin of a wearer (e.g., joining leg cuffs of a diaper or a waist cuff of a diaper to the body of the wearer for improved gasketing to reduce leakage of fluids such as urine).

Figure 18A:
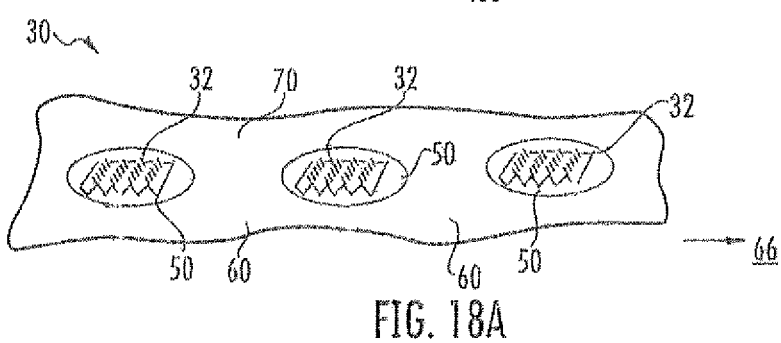
FIGS. 18A-18C illustrate patches of synthetic setae on base layers of various topographies as may be utilized in an adhesive fastener.

FIG. 18A illustrates an embodiment of an adhesive material 30. Here shown as a tape-like length of a thin, flexible base layer 70 onto which has been disposed spaced apart, discrete patches 50 comprising a substrate including a plurality of synthetic setae 32, with substantially setae free regions 60 of the base layer separating the patches 50. The patches 50 can include a three dimensional material including the extended setae laminated with a backing sheet. Alternatively, a three dimensional material alone can form a patch 50, with no separately formed and attached backing sheet between the material and the base layer 70 onto which the three dimensional material has been adhered.

The patches 50 are spaced apart in a first direction 66 of the base layer 70, which may be the machine direction or may be the direction in which the base layer 70 is most extensible. The substrate may be elastomeric, or may be a creped or foreshortened material which can be stretched in one or more directions, but does not necessarily retract substantially when the extensional force applied to the base layer 70 is relaxed. If the base layer 70 is substantially elastic, it may, for example, be extended in a direction by about 20% of its initial length upon application of a predetermined extensional force in that direction, and then, upon removal of the extensional force, retract to a length no greater than about 10% longer than its initial length.

In general, patches 50 including setae 32 can move apart when the base layer 70 is stretched. The base layer material may be readily stretchable in one or more directions, and may be planar, three-dimensional, porous, non-porous, fibrous, a film, and may comprise apertures. The base layer 70 may also have a three-dimensional texture.

Figure 18B:
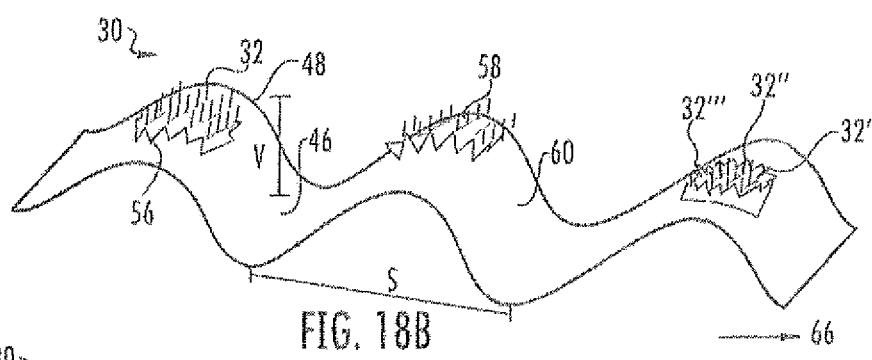

FIG. 18B depicts an embodiment of an adhesive material 30 having a three-dimensional topography characterized by a series of peaks 48 and valleys 46, with a characteristic valley depth V (elevation difference between the peaks and the valleys), spaced apart with a characteristic spacing S between successive valleys. Here the peaks and valleys alternate in a first direction 66 (which may be the machine direction or another direction). As shown, the synthetic setae 32 are grouped together in a plurality of groups, such as a first group 56 and a second group 58, with a substantially setae free region 60 disposed between the groups 56, 58.

Figure 18C:
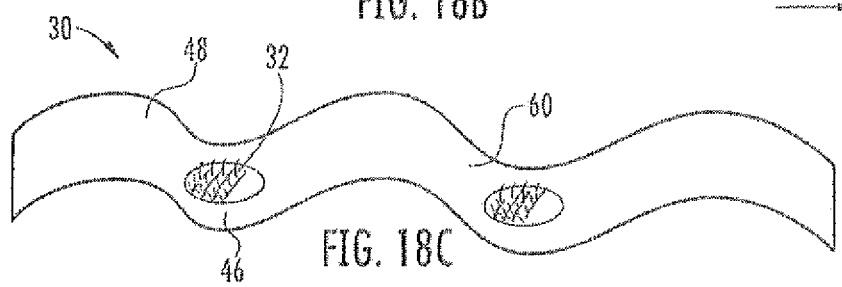

As depicted, the groups 56, 58 may be selectively disposed on the peaks 48 of the substrate, or alternatively may be selectively disposed on valleys 46 of the substrate (FIG. 18C). Alternatively, the groups 56, 58 may be spaced apart at a spacing other than the characteristic spacing S between successive valleys 46, such that some groups fall on the peaks 48 and others fall on the valleys.

FIG. 18C shows an adhesive material 30 similar to that of FIG. 18B, except that the setae 32 are selectively located in the valleys 46, and the peaks 48 are generally part of the setae free regions 60. In this embodiment, the setae 32 may be protected from contamination with other materials until pressed into contact with an opposing surface (not shown). Stretching of the adhesive material 30 may also be applied to raise the valleys 46 with respect to the peaks 48, thus making the adhesive setae 32 more easily accessible for adhesion to opposing surfaces.

Patches including setae may be protected with a removable cover to protect them from premature adhesion or contamination, similar in principle to a silicone-coated release paper that is commonly placed over pressure-sensitive adhesive regions in absorbent articles to prevent premature adhesion. The removable cover may be a paper strip coated with a silicone-based material, a fluoropolymer, a wax, or other material capable, or may be a film or other web.

Figure 19A:
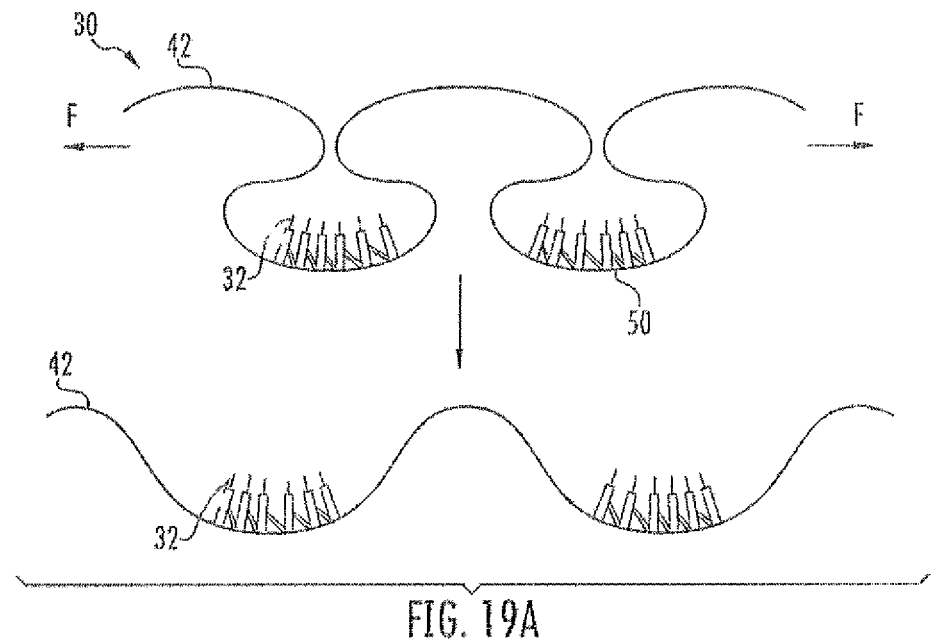
FIGS. 19A-19B illustrate side views of fasteners incorporating disclosed adhesive materials.

For example, and with reference to FIG. 19A, patches 50 including setae 32 can be placed on a substrate 42 in such a way that they are hidden inside the valleys or grooves on a substrate surface. These grooves can be designed to protect the setae from contaminants during the manufacturing process, e.g., the process of putting together an absorbent article. When in use, adhesive material can be activated by applying a moderate stretch in the direction perpendicular to the direction of the grooves. The stretch can open up the grooves and makes the adhesive setae available for interaction with the attachment surface (not shown).

Figure 19B:
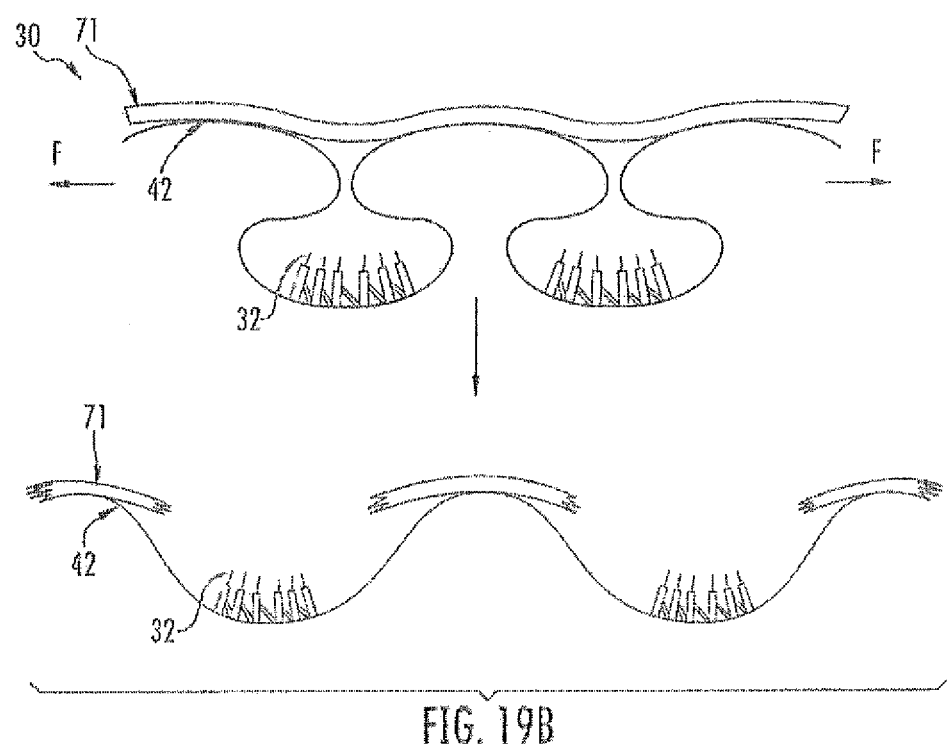

Another example is presented on FIG. 19B. In this example a substrate 42 with patches of the adhesive setae 32 attached to it is laminated to a thin film 71 that provides additional protection for adhesive setae while not in use.

The activation mechanism can include stretching of the substrate in the direction perpendicular to the grooves, which results in breaking of the protective film. This releases adhesive setae and makes them available for the interaction with the attachment surface. Besides providing the benefit of contamination resistance, examples presented in FIG. 19A and FIG. 19B also have an advantage of not engaging with unwanted surfaces such as, for example, baby or caregiver clothes, etc.

Figure 20:
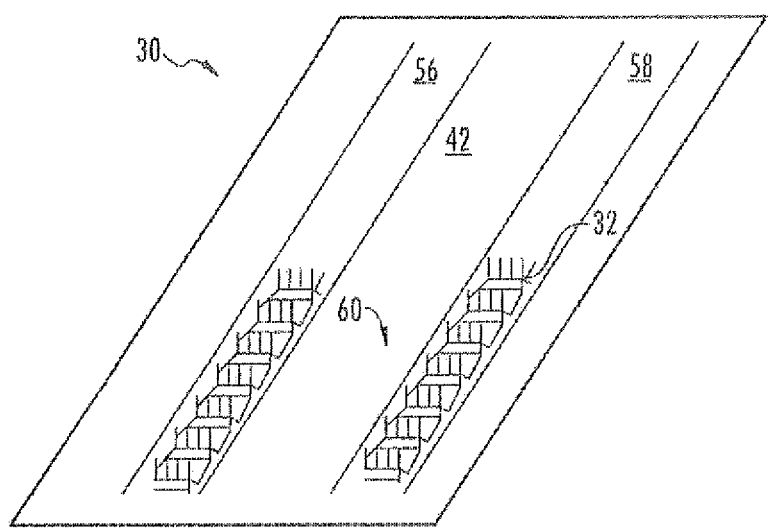
FIG. 20 illustrates a section of an adhesive material including areas of synthetic setae in conjunction with non-adhesive areas.

FIG. 20 depicts a section of an adhesive material 30 in which a large patch including setae 32 is located on a substrate 42 such that the setae 32 are disposed in distinct groups 56, 58 separated by setae-free regions of the substrate 42. The setae free region 60 may have a width of about 1 micron or greater, such as about 5 microns or greater, about 10 microns or greater, or about 20 microns of greater, with exemplary ranges of from about 5 microns to about 100 microns, or from about 15 microns to about 200 microns.

In another embodiment, the planar substrate that defines one or more linear arrays of setae can also define one or more setae free regions between areas of setae. Following manipulation of the planar substrate to rotate and extend the setae out of the plane of formation, the setae free regions of the planar substrate can function as a flexible base layer that can support the setae. For instance, the base layer can be utilized to bond the adhesive material to a product such as a diaper, a training pant, or the like and utilize the adhesive material as a closure.

Figure 21:
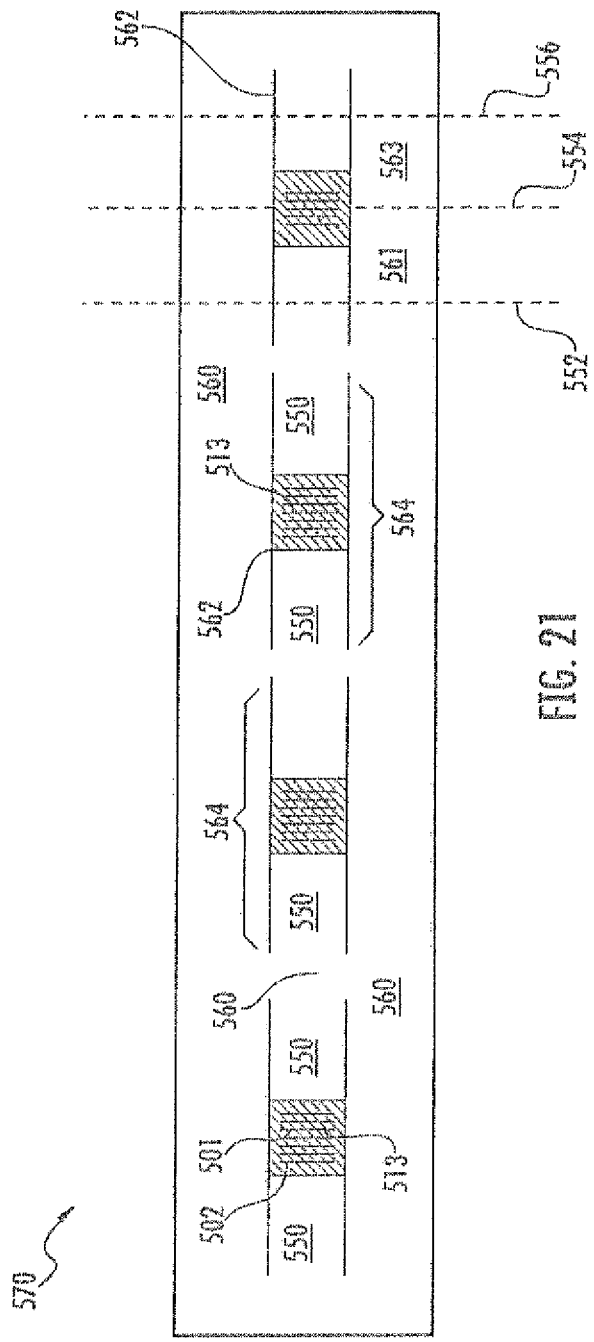
FIG. 21 illustrates another embodiment of a planar substrate including areas defining linear arrays of synthetic setae.

Referring to FIG. 21, a planar substrate 570 is illustrated. The planar substrate has been formed so as to include setae free region 560 as well as strips 564. Each strip 564 includes an area 513 that defines laterally extending supports 501 and a plurality of setae 502 along each laterally extending support 501 as well as a support structure 550 on either side of an area 513. At the terminus of each support structure 550, the support structure 550 meets the setae free region 560. The planar substrate 570 also includes cuts 562 that allow for the folding of the planar substrate 570 into a three dimensional adhesive material.

The setae free region 560 can be folded along fold lines 552, 554, 556 to form the three dimensional material and rotate and extend the setae 502 out of the plane of formation. More specifically, each strip 564 is associated with three fold lines 552, 554, and 556 that extend across the setae free region 560 on either side of a strip 564. The setae free region 560 can be folded at each strip such that fold line 552 meets fold line 556. Upon folding, the setae free region 561 between fold lines 552 and 554 and the setae free region 563 between fold lines 554 and 556 can be folded down out of the plane of formation along the fold lines and this folding can cause the strip 564 to extend up out of the plane of formation.

Figure 22:
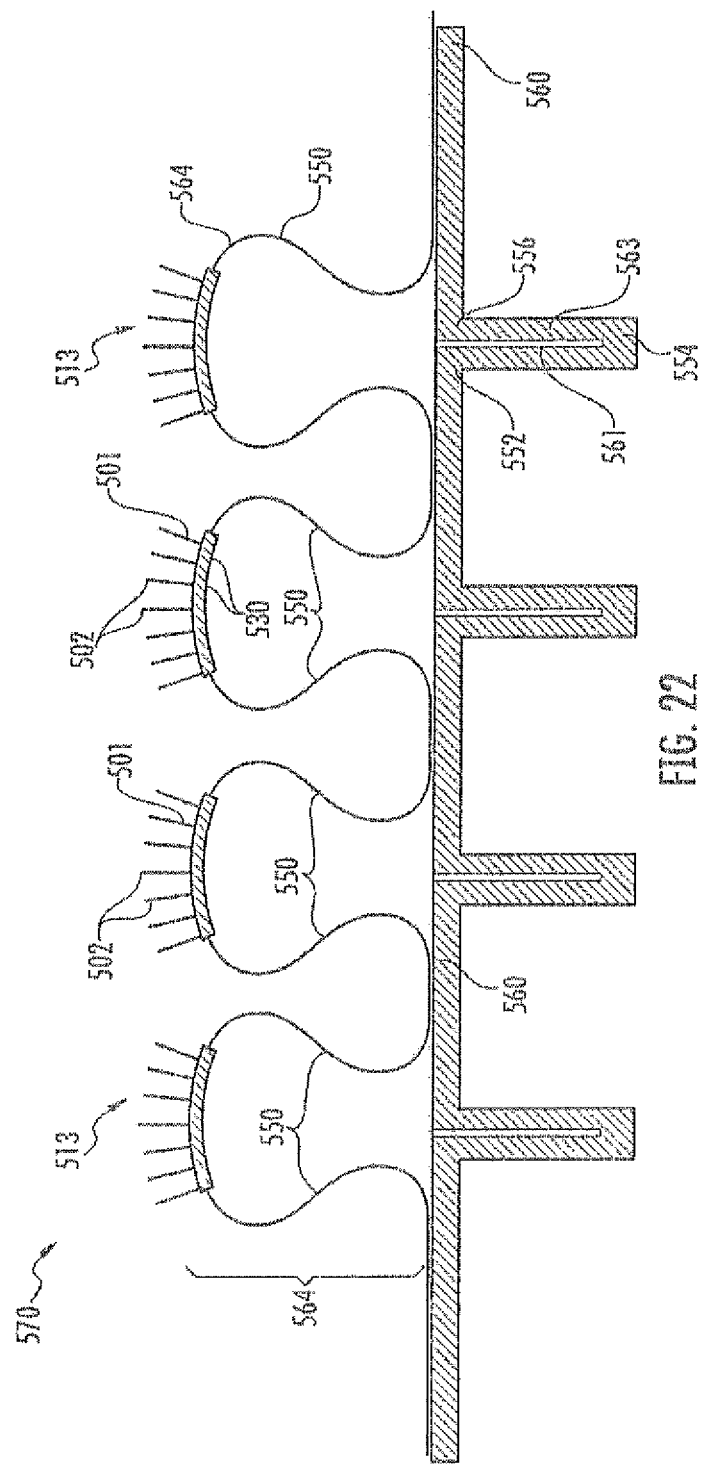
FIG. 22 illustrates the substrate of FIG. 21 following manipulation to extend the setae in an outwardly direction from the plane of formation.

FIG. 22 is a side view of the substrate 570 following the folding process. As can be seen, the setae free region 560 has been folded such that fold line 552 meets fold line 556 and setae free regions 561 and 563 extend down beneath the plane of formation. In addition, strips 564 extend up out of the plane in a loop formation. The loop includes a support structure 550 on either side of an area 513 that defines a plurality of setae 502. As the strips 564 are extended up and out of the plane of formation in forming the loop, the laterally extending supports 501 and linear arrays of setae 502 thereon can be rotated to extend outwardly from the plane of formation of the area 513. In FIG. 22, each linear array is seen from the end, hence, each linear array is designated by a seta 502 at the terminal end of each array. In this view, the connecting members 530 between each adjacent laterally extending support can also be seen. The setae free region 560 can then function as a flexible base layer for attachment of the adhesive material to a product.

Figure 23:
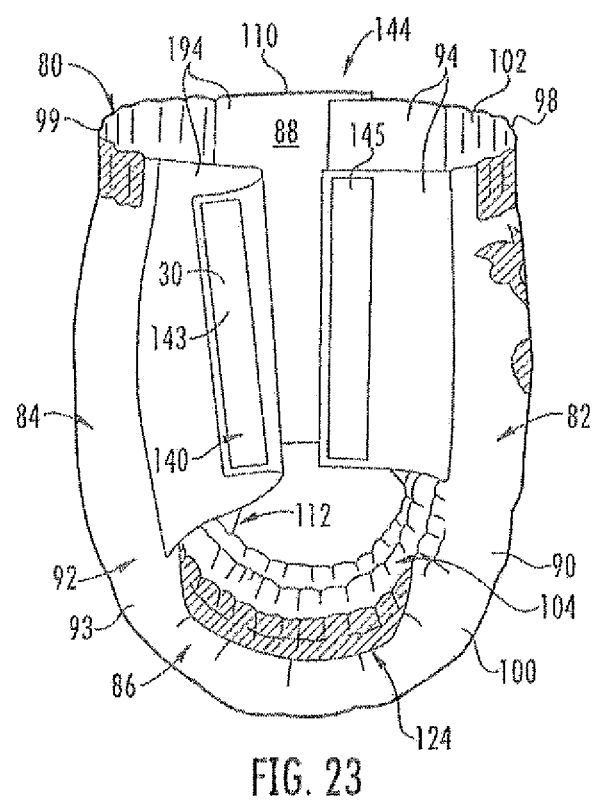
FIG. 23 is an absorbent article in the form of a training pant including an adhesive material as described herein.

As shown in FIG. 23, a disposable absorbent article 80, here depicted as a training pant, can comprise the adhesive material 30 according to the present disclosure. The absorbent article 80 is related to the training pant of U.S. Pat. No. 6,562,167 to Coenen et al. It is illustrated in a partially fastened mode in FIG. 23. The absorbent article 80 comprises an absorbent chassis 92 and a fastening system 140 having a strip of adhesive material 30. The absorbent chassis 92 defines a front waist region 82, a back waist region 84, a crotch region 86 interconnecting the front and back waist regions, an inner surface 88 which is configured to contact the wearer, and an outer surface 90 opposite the inner surface which is configured to contact the wearer's clothing. The absorbent chassis 92 also defines a pair of transversely opposed side edges and a pair of longitudinally opposed waist edges, which are designated front waist edge 98 and back waist edge 99. The front waist region 82 is contiguous with the front waist edge 98, and the back waist region 84 is contiguous with the back waist edge 99.

Figure 24:
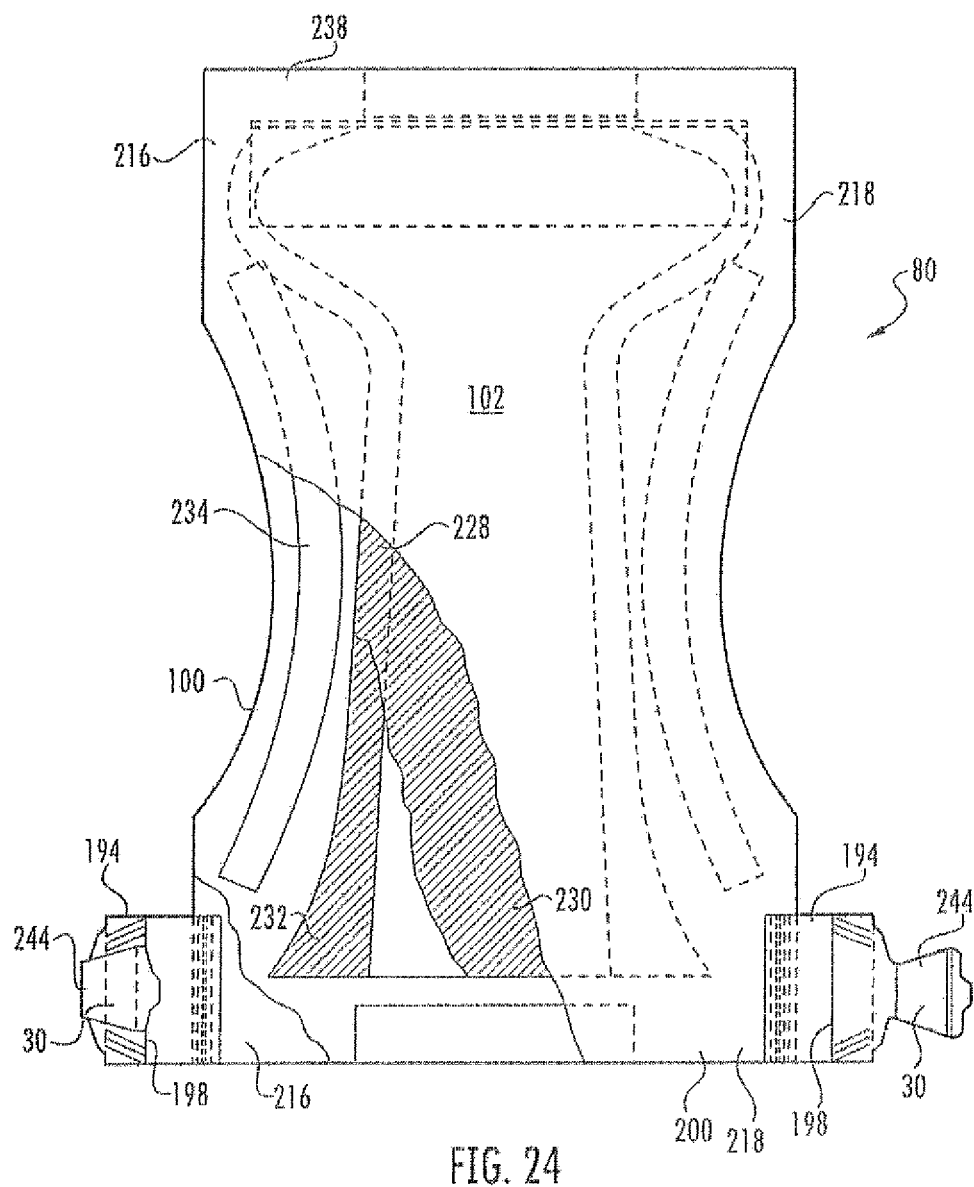
FIG. 24 is an absorbent article in the form of a disposable diaper including an adhesive material as described herein.
Figure 25:
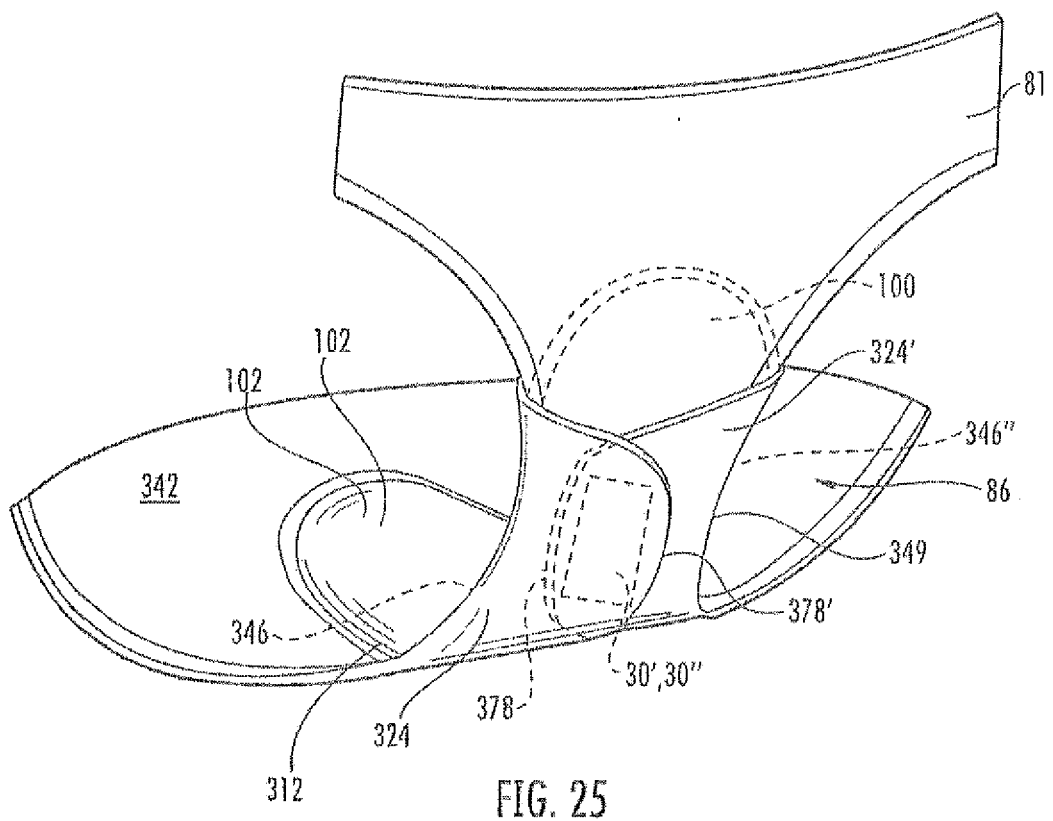
FIG. 25 is an absorbent article in the form of a feminine care product including an adhesive material as described herein.

The illustrated absorbent chassis 92 comprises a composite structure 93 which can be rectangular or any other desired shape, a pair of transversely opposed front side panels 94, and a pair of transversely opposed back side panels 194. The composite structure 93 and side panels 94 and 194 may comprise two or more separate elements, as shown in FIG. 24, or may be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant, which may further comprise segments of gecko-like adhesive material (not shown) disposed on the outer surface thereof.

The absorbent article 80 and in particular the outer cover 100 may comprise one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and so forth in the product; registering a back label, or a front label, in the product; and registering written instructions at a desired location in the product. Graphics depicting geckos or gecko feet or depicting the adhesive power of gecko feet (e.g., an image of gecko adhering to a flat surface) may be displayed on the article to convey its novel adhesive functionality.

The appearance-related components may be positioned on an absorbent article at selected locations, which can be carried out using the methods disclosed in U.S. Pat. No. 5,766,389 to Brandon et al., which is incorporated herein by reference. The primary pictorial image may be positioned in the front waist region 82 along the longitudinal center line of the absorbent article 80.

The illustrated absorbent article 80 includes a fastening system 140 for refastenably securing the training pant about the waist of the wearer. The illustrated fastening system 140 includes first fastening components (not shown) and 143 that are adapted to refastenably connect to mating second fastening components 144 and 145. When the first fastening components comprise gecko-like adhesive material 30, as shown, the second fastening components can comprise material joined to the front side panels 94 or may simply be the outer cover 100 itself or any existing functional component of the absorbent article 80, in which case the second fastening components may simply be regions of other materials onto which the first fastening components 143 can be attached. Alternatively, the second fastening components may comprise materials particularly suited for attachment to gecko-like adhesive setae, such as a textured hydrophobic web or smooth hydrophobic film of known compatibility with the materials of the adhesive material 30 (simple adhesive testing can be done to select a suitable material for the second fastening components). Alternatively, the second fastening components may also comprise regions of gecko-like adhesive material 30 (not shown).

FIG. 24 depicts another example of an absorbent article 80, in this case a disposable diaper in which at least one strip of adhesive material 30 is used. Apart from the use of gecko-like adhesive material 30, much of the design of the chassis and other components of the absorbent article 80 is disclosed by U.S. Pat. No. 5,399,219 to Roessler et al., herein incorporated by reference in its entirety.

The article includes a fastening means, such as a fastening assembly 244 that is connected to each of the stress beam sections 198 and is arranged to extend laterally from each of the side panels 194 for securing the waistband sections of the article about a wearer during the use of the article. In various embodiments of the invention, a fastening assembly 244 can be located at either or both of lateral end regions 216 and 218 of either or both of waistbands 238 and 200, respectively. The representatively shown embodiment has the fasteners located at the terminal side edges of rear waistband 200. The fastening assembly 244 can be bonded to the absorbent article 80 by any known means such as by ultrasonically welded bonds, thermal welds, adhesives, and so forth, and one or more layers of additional material serving as tab substrates or bonding means, which may also enhance strength, stretching properties, or other features.

The fastening assembly 244 employs at least one section of adhesive material 30 with gecko-like functionality. Because the adhesive material 30 may be more flexible than conventional mechanical fastening means and can be made to be integral with the outer cover 100 or with the side panels 194 (i.e., the substrate of the adhesive material 30 can be the same material as the outer cover 100 or side panels 194), a simplified design can be used (not shown) in which the side panels 194 and fastening assemblies 244 are substantially extensions of the outer cover 100 material or joined to the outer cover 100 material with a single seam or bond.

In one example, the adhesive material 30 comprises an elastomeric substrate (not shown) or is joined to an elastomeric side panel, such that the fastening assembly 244 can be stretched during attachment and detachment to somewhat imitate the peeling of setae from an attached surface as a gecko curls its toes when lifting a foot away from a surface. The adhesive setae (not shown) can be positioned or angled for good attachment when a stretched side panel is relaxed after being put into place, and for good detachment when the side panel is stretched again and lifted. In one example, all or a portion of the adhesive setae have an angle of inclination such that they lean toward the longitudinal centerline of the article (e.g., the tops of the adhesive setae are generally slightly close to the longitudinal centerline than the bases of the respective adhesive setae) when the absorbent article 80 is not attached, as in FIG. 24.

To provide a refastenable adhesive taping system, the absorbent article 80 may include a supplemental landing zone patch 246, which provides a target zone for receiving an attachment of fastener assembly 244 thereon. In the illustrated example of the invention, landing zone patch 246 is positioned on the outward surface of the outer cover 100 and is located on the second, front waistband portion 238 of the absorbent article 80. The landing zone patch 246 is constructed of a suitable material, such as polypropylene, polyester, or the like, and is configured and arranged to accept a secure adhesion of fastener assemblies 244. In addition, the landing zone patch 246 and the fastener assemblies 244 are cooperatively constructed and arranged to provide a releasable adhesion which allows the fastener assemblies 244 to be removed from the landing zone patch 246 for repositioning and re-adhesion without tearing or excessively deforming the material of the outer cover 100. For example, a suitable tape landing zone construction is described in U.S. Pat. No. 4,753,649 to Pazdernik, the disclosure of which is hereby incorporated by reference to the extent that it is consistent herewith.

Another location suitable for further placement of adhesive material 30 of the present invention is over leg cuffs (not shown) or other cuffs, including on the bodyside liner 102 substantially over the leg elastic members 234 to join the absorbent article 80 to the body of the wearer for improved gasketing. The adhesive material 30 may also be used to join the absorbent article 80 to other external items such as printed webs (not shown) with graphics that can be attached and removed from the outer cover 100 to provide customizable or removable graphics. Other components that could be attached to the absorbent article 80 with adhesive material 30 means could include biosensor components and so forth.

In particular aspects, each of the side panels 194 may be formed from a separate piece of material which is then suitably assembled and attached to the selected front and/or rear waistband portion of the absorbent article 80. In the illustrated embodiments of the invention, for example, side panels 194 are attached to the rear waistband portion of the outer cover 100, and may be operably attached to either or both of the outer cover 100 and bodyside liner 102 components of the article. The side panels extend laterally to form a pair of opposed waist-flap sections of the absorbent article 80, and are attached with suitable connecting means, such as adhesive bonding, thermal bonding, ultrasonic bonding, clips, staples, sewing or the like, or may be attached with removable fastening means (not shown) such as gecko-like adhesive material.

The adhesive material 30 may also be used in sanitary napkins, such as those disclosed in U.S. Pat. No. 5,681,303 to Mills et al., which is incorporated herein by reference thereto for all relevant purposes. Particular attention is called to FIGS. 2, 3, and 4 of U.S. Pat. No. 5,681,303, in which central pad adhesives or flap adhesives or both can be replaced with gecko-like adhesive material 30 to provide improved attachment to undergarments. Protective release paper or film may also be provided, if desired, to protect the adhesive material 30 when not in use. Release liners that also serve as an individual package for a sanitary napkin are described in U.S. Pat. No. 4,556,146 to Swanson, et al. and WO 91/18574.

Another configuration of feminine care products which may benefit from the use of gecko-like adhesive materials is shown in U.S. Pat. No. 4,917,697 to Osborn, III et al. The adaptation of gecko-like adhesive technology to such an article is illustrated in FIG. 17 of Osborn, III et al.

The absorbent article 80 (here a sanitary napkin) is utilized by removing any release liners (if present) and thereafter placing the absorbent article 80 in a panty 81 as shown in FIG. 24. The center of central absorbent pad 312, which lies between the outer cover 100 and the bodyside liner 102 of the absorbent article 80, is placed in crotch portion 86 of the panty 81 with one end of central absorbent pad 312 extending towards the front section 340 of the panty and the other end towards the back section 342 and with the outer cover 100 in contact with the inner surface of center crotch portion 86 of the panty. A central section of adhesive material 30 maintains the central absorbent pad 312 in position. The distal portions of flaps 324 and 324' are folded around, respectively, side edges 346 and 346'. Patches of gecko-like adhesive material 30', 30" serve as flap fasteners to secure flaps 324 and 324' in such position. Thus, flaps 324 and 324' are each folded over themselves with a portion of the panty, including side edges 346 and 346', interposed therebetween. The flaps are folded over a fold line 349 defined by the edge of the panty 81 in the crotch region 86. As shown, the central section of adhesive material 30 is disposed between the outer cover 100 of the absorbent article 80 beneath the central absorbent pad 213 and the bodyside surface of the panty 81, while the patch of adhesive material 30', 30" on the flaps 324, 324' are the garment side of the panty 81, with one patch of adhesive material 30' being against the panty 81 itself, joining it to a flap 324', and the other patch of adhesive material 30" joining one flap 324 to the other flap 324'. The adhesive material 30', 30" may extend up to or near the distal edges 378, 378' of the flaps, if desired.

Numerous other sanitary napkin embodiments having flaps are available and are disclosed in the literature. For example, sanitary napkins having flaps are disclosed in U.S. Pat. No. 4,687,478 to van Tilburg, U.S. Pat. No. 4,608,047 to Mattingly, U.S. Pat. No. 4,589,876 to van Tilburg, U.S. Pat. No. 4,285,343 to McNair, U.S. Pat. No. 3,397,697 to Rickard, and U.S. Pat. No. 2,787,241 to Clark.

Gecko-like adhesive material can also be used to attach flapless absorbent articles such as sanitary napkins and pantiliners to the undergarments. In such cases, pressure-sensitive adhesives or non-skid material usually applied to a side of the absorbent article can be replaced or supplemented with gecko-like adhesive material. Examples of flapless sanitary napkins and pantiliners are presented in U.S. Pat. No. 4,834,739 to Linker, III et al., and U.S. Pat. No. 5,011,480 to Gossens et al.

It will be appreciated that the foregoing examples, given for purposes of illustration, are not to be construed as limiting the scope of this invention. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. An adhesive material comprising:
   a first laterally extending support and a first plurality of setae extending outwardly therefrom;
   a second laterally extending support that is adjacent to the first laterally extending support in a longitudinal direction, a second plurality of setae extending outwardly from the second laterally extending support;
   wherein the setae define three or more hinges and contain a stalk and a spatula that extends from the stalk, wherein the stalk has a length of from about 50 nanometers to about 500 micrometers and a width of from about 10 nanometers to about 50 micrometers, and wherein the spatula has a length of from about 20 nanometers to about 20 micrometers and a width of from about 2 nanometers to about 1 micrometer;
   wherein the first and second laterally extending supports are either directly or indirectly connected to one another.

2. The adhesive material of claim 1, wherein the first and second laterally extending supports are indirectly connected to one another, the adhesive material further comprising a connection member that extends from the first laterally extending support to the second laterally extending support to indirectly connect the first and second laterally extending supports.

3. The adhesive material of claim 2, at least a portion of the connection member being at an angle relative to the longitudinal direction.

4. The adhesive material of claim 3, wherein the angle of at least a portion of the connection member relative to the longitudinal direction is from about 10° to about 90°.

5. The adhesive material of claim 2, wherein the connection member extends from an edge of the first laterally extending support to an edge of the second laterally extending support.

6. The adhesive material of claim 2, wherein the connection member extends from an opposing edge of the first laterally extending support to an opposing edge of the second laterally extending support.

7. The adhesive material of claim 1, wherein the first laterally extending support and the second laterally extending support are directly bonded to one another.

8. The adhesive material of claim 1, wherein the stalk has a width of from about 10 nanometers to about 50 micrometers and a length of from about 1 micrometers to about 300 micrometers.

9. The adhesive material of claim 1, wherein the spatula has a width of from about 2 nanometers to about 1 micrometer and a length of from about 50 nanometers to about 15 micrometers.

10. The adhesive material of claim 1, wherein the stalk varies in cross section along the length of the stalk.

11. The adhesive material of claim 1, wherein the setae define one or more hinges.

12. The adhesive material of claim 1, wherein each seta comprises from about 3 to about 2500 spatulae.

13. The adhesive material of claim 1, wherein the adhesive material comprises a loop structure, the first plurality of setae extending outwardly from the loop structure.

14. The adhesive material of claim 1, wherein the center to center spacing between two adjacent setae is from about 2 to about 30 micrometers.

15. The adhesive material of claim 1, wherein the first plurality of setae form a linear array.

* * * * *